United States Patent [19]

Slimak

[11] Patent Number: 5,234,706
[45] Date of Patent: Aug. 10, 1993

[54] PROCESSES FOR PRODUCTS FROM POTATOES AND OTHER ROOTS, SEEDS, AND FRUIT

[76] Inventor: K. M. Slimak, P.O. Box 2444, Springfield, Va. 22152

[21] Appl. No.: 696,086

[22] Filed: May 6, 1991

Related U.S. Application Data

[63] Continuation-in-part of Ser. No. 522,820, May 14, 1990, which is a continuation-in-part of Ser. No. 825,656, Jan. 31, 1986, Pat. No. 4,925,697, which is a continuation-in-part of Ser. No. 294,690, Aug. 1, 1988.

[51] Int. Cl.⁵ .................................................. A23L 1/214
[52] U.S. Cl. ........................................ 426/549; 426/550; 426/552; 426/562; 426/518; 426/524; 426/601; 426/637
[58] Field of Search ............... 426/562, 601, 550, 637, 426/549, 518, 523, 524, 552, 801, 804

[56] References Cited

U.S. PATENT DOCUMENTS

| | | |
|---|---|---|
| Re. 29,773 | 10/1978 | Wisdom et al. ................ 426/49 |
| 38,039 | 3/1863 | Frost . |
| 77,995 | 5/1868 | Marshall . |
| 91,554 | 6/1869 | Marshall . |
| 100,587 | 3/1870 | Baylor . |
| 125,247 | 4/1872 | Adamson et al. . |
| 310,927 | 1/1885 | Whitcomb . |
| 592,906 | 11/1897 | Gere ................................ 426/640 |
| 1,119,849 | 12/1914 | Malcolm . |
| 1,151,805 | 9/1915 | Ray . |
| 1,193,828 | 8/1916 | Sattler . |
| 1,194,455 | 8/1916 | Williams . |
| 1,238,371 | 8/1917 | Williams . |
| 1,470,929 | 10/1923 | Li . |
| 1,571,945 | 3/1926 | Heimerdinger ................ 426/550 |
| 1,676,160 | 7/1928 | Ruffner . |
| 2,168,246 | 8/1939 | Shepherd . |
| 2,469,995 | 12/1946 | Schaul . |
| 2,687,960 | 8/1954 | Sharp . |
| 3,162,536 | 12/1964 | Kaufmann . |
| 3,208,855 | 9/1965 | Enoch et al. . |
| 3,346,390 | 10/1967 | Pichel et al. . |
| 3,394,012 | 7/1968 | Kolton et al. . |
| 3,493,390 | 2/1970 | Succo ............................... 99/100 |
| 3,497,360 | 2/1970 | Schaefer et al. . |
| 3,615,658 | 10/1971 | Glabe ............................... 99/17 |
| 3,762,423 | 12/1973 | Tsantir et al. ................... 426/62 |
| 3,767,424 | 10/1973 | Schimizu et al. ............... 426/372 |
| 3,881,028 | 4/1975 | Caposella, Jr. et al. ....... 426/242 |
| 4,028,469 | 6/1977 | Kritchevskt et al. .......... 426/551 |
| 4,109,018 | 8/1978 | Thompson ..................... 426/62 |
| 4,277,510 | 7/1981 | Wicklund et al. ............. 426/441 |
| 4,283,425 | 10/1981 | Yaun et al. ..................... 426/102 |
| 4,520,034 | 5/1985 | Ishii et al. ...................... 426/96 |
| 4,565,705 | 1/1986 | Snider ............................ 426/270 |
| 4,749,574 | 6/1988 | Haydock et al. .............. 426/242 |
| 4,756,916 | 7/1988 | Dreher et al. ................. 426/302 |
| 4,853,236 | 8/1989 | Langler ......................... 426/102 |
| 4,906,483 | 3/1990 | Kloos ............................ 426/243 |
| 4,917,908 | 4/1990 | Prosise ......................... 426/102 |
| 4,917,909 | 4/1990 | Prosise ......................... 426/102 |
| 4,919,965 | 4/1990 | Childers, Jr. ................. 426/615 |
| 4,933,199 | 6/1990 | Neel et al. ..................... 426/438 |

FOREIGN PATENT DOCUMENTS

| | | |
|---|---|---|
| 1517050 | 8/1974 | Fed. Rep. of Germany . |
| 2950315 | 6/1981 | Fed. Rep. of Germany . |
| 3141174 | 4/1983 | Fed. Rep. of Germany . |
| 1395654 | 2/1965 | France . |
| 2574633 | 6/1986 | France . |
| 104850 | 8/1980 | Japan .............................. 426/637 |

OTHER PUBLICATIONS

Ware "Possibilities in new & extended uses of the sweet potato" Alabama Agricultural Experimental Station 1941 p. 9.

(List continued on next page.)

*Primary Examiner*—R. B. Penland
*Attorney, Agent, or Firm*—Stevens, Davis, Miller & Mosher

[57] ABSTRACT

A variety of different food products, prepared from edible roots, seeds, and starchy fruits including potatoes, arrowroot, water chestnut, jicama, buckwheat, legumes, millet, milo, barley, oats, corn, teff, rice, cotton seed meal, bread fruit, pumpkin, winter squash, white squash, plantain, banana, and jack fruit are substitutes for wheat and other grains, milk, eggs, and a partial substitute for nuts. A variety of starches, soluble fibers, and insoluble fibers may be combined to provide products that are substitutes for wheat and other grains, milk, eggs, and a partial substitute for nuts.

18 Claims, No Drawings

OTHER PUBLICATIONS

Van de Mark "Alamalt-its properties & uses" Alabama Agricultural Experimental Station 1945 pp. 1-5.

Webster "Third New International Dictionary" P B Grove (Editor) Merriam Co Publishers (1961) pp. 322, 500, 875, 2310 & 2459.

Bouwkamp "Sweet Potato Products: A natural resource of the Tropics" CRC Press Inc pp. 137, 185-218, 255-258 (1985).

Soukhanov, Anne H., ed, Webster's II New Riverside University Dictionary, Riverside Publishing Company, Boston, MA, 1984, p. 1132.

Craeco "Tubers: composition & use in bread making" Dissertation Abstracts Int B (1977) 38 (4) p. 1480.

Casier et al Bread Production from pure flours of tropical starchy crops Tropical Foods Chem & Nutrit Academic Press NY vol. 1 (1979) pp. 279-340.

Snack Food Journal Feb. 1980 p. 20.

Bailey et al., Hortus Third, MacMillan Publishing Co., Inc., New York, pp. 683, 993, 773, 772, 757.

Beattie, W. R., 1908, Sweet Potatoes, Government Printing Office, Washington, pp. 34-37.

Bell et al., 1980, Effect of Traditional Food Processing Methods on the Nutritional Value of Yams in Camaroon in Tropical Root Crops: Research Strategies for the 1980s, ed. Terry et al., Nigeria, 218.

Bender, A. E., 1975, Dictionary of Nutrition and Food Technology, Chemical Publishing Co., Inc., New York, pp. 84-85.

Casier, J. P. J., 1975, Effect of Water Insoluble Endosperm Pentosans of Wheat and Rye on the Dough and Baking Properties of Soft Wheat and Other Starch Rich Materials such as Manioc, Sorghum, Millet, etc., Fermentation, 71:3, pp. 117-134.

Cassava Processing, 1977, The Food and Agriculture Organization of the United Nations, pp. 3, 12-15, 20-21, 84-85, 93-94.

Corwin, A. H., 1976, The rotating diet and taxonomy, in Clinical ecology, Dickey, L. H., ed., Charles C. Thomas Publisher, pp. 126-133.

Crabtree et al., 1978, The breadmaking potential of products of cassava as partial replacements for wheat flour, J. Fd. Technol, vol. 13, pp. 397-407.

de Caloni et al., 1984, Elaboration and evaluation of typical Puerto Rican dishes prepared with mixtures of plantain, cassava and tanier flours, Jan. 1984, pp. 67-74. Food Engineering, pp. 250-262.

Ensminger et al., 1983, Foods and nutrition encyclopedia, vol. 1 A-H, p. 2359.

Erdman, M. D., 1986, Starch from arrowroot (*Maranta arundinacea*) grown at Tifton, Georgia, Cereal Chemistry, 63: 3, pp. 277-279.

Faure et al., 1974, Production and marketing of composite flour bakery goods in developing countries, Procedures of the Fourth International Congress of Food Science and Technology, vol. 5, pp. 231-242.

Food composition tables for use in the English speaking Caribbean, 1974, The Caribbean Food and Nutrition Institute, Kingston, Jamaica, pp. 14-16.

Gleason, et al., Manual of vascular plants of Northeastern United States and adjacent Canada, D. van Nostrand Co., Inc., New York, p. 301.

Hudson et al., 1976, The effects of fibre, starch damage and surfactants on the baking quality of wheat/cassava composite flours, Journal of Food Technology, 2:2, pp. 129-136.

Yoshitaro, T., ed., 1942, Kenkyusha's new Japanese-=English dictionary, Harvard university press, Cambridge, Massachusetts, pp. 883, 884, 1586, 1587, 2152, 2153.

Martin et al, 1974, Flours made from edible yams (*Dioscorea* spp.) as a substitute for wheat flour, Journal of Agriculture of University of Puerto Rico, pp. 255-263.

Martin, G. et al., 1983, Introduction of flour from *Dioscorea dumetorum* in a rural ara, in Tropical root crops: production and uses in Africa, Proceedings of the Second Triennial Symposium of the International Society for Tropical Root Crops, Camaroon, pp. 161-163.

Morrison, F., 1957, Feeds and feeding: a handbook for the student and stockman, The Morrison Publishing Co., Ithaca, New York, pp. 390-393, 556-557.

New Riverside University Dictionary, 1984, Houghton Mifflin Co., Boston, Massachusetts, p. 1132.

The Oxford English dictionary, 1933, Oxford University Press, vol. 8, pp. 1315, 1318.

Peterson et al., 1968, A field guide to the wildflowers of Northeastern and Northcentral North America, Houghton Mifflin C., Boston, Massachusetts, pp. 6 and 8.

OTHER PUBLICATIONS

Pulle et al., 1975, Physico-chemical characteristics of composite flours, Journal of Milk Food Technology, 38:7, pp. 401–405.

Raja et al., Studies on improving the textural quality of cassava (Tapioca) flour, pp. 108–116.

Rodriguez-Sosa et al., 1983, Amylography of plantain, cassava, and tanier flours, Journal of Agriculture of the University of Puerto Rico, pp. 303–311.

Sanchez-Marroquin, A., 1983, Two forgotten crops of agroindustrial importance; amaranth and quinoa, Arch. Latinoam, Nutr. 33:1, 11–32 (abstract 99(1983) Sep., No. 13, Columbus, Ohio, USA).

Sanchez-Marroquin et al., 1985, Amaranth flour blends and fractions for baking applications, Journal of Food Science, vol. 50, pp. 789–794.

Sanchez-Marroquin et al., 1985, Industrial corn flour enrichment with whole amaranth flour and milling fractions in corn based products, Archivos Lationamericanos de Nutricion, 35:3, pp. 518–535.

Talburt et al., 1959, Potato processing, The Avi Publishing Co., Inc., Westport, Connecticut, pp. 390–391.

Teutonico et al., 1985, Amaranth: composition, properties and applications of a rediscovered food crop, Food Technology, 39:4, pp. 49–61.

Agriculture Handbook No. 457, 1974(?), Tropical yams and their potential, part 1. *Dioscorea esculenta*, pp. 16–18.

Watt et al., 1963, Composition of foods: raw, processed, prepared, Agriculture Handbook No. 8, United States Department of Agriculture, Washington, D.C., pp. 66, 51.

Weber, E. 1978, The Inca's ancient answer to food shortage, Nature, vol. 272, p. 486.

Gove, P. et al., 1961, Webster's third new international dictionary of the English language, unabridged, Merriam Webster Inc., Springfield, Mass., pp. 52, 72, 109, 121, 288, 289, 322, 347, 500, 637, 784, 875, 947, 1339, 1351, 1365, 1553, 1960, 2310, 2341, 2459, 2460, 2646, 2647.

Winton, et al., 1935, The structure and composition of foods, vol. 11, Vegetables, legumes, and fruits, John Wiley and Sons Inc., New York, pp. 120–123.

Yanez et al. 1986, Amaranthus hypochondriacus: starch isolation and partial characterization, Cereal Chemistry, 634:3, pp. 273–277.

PROCESSES FOR PRODUCTS FROM POTATOES AND OTHER ROOTS, SEEDS, AND FRUIT

RELATED APPLICATIONS

The present application is a continuation in part of patent application Ser. No. 522,820, filed on May 14, 1990, titled, "Processes for Products from Sweet Potato", the entire disclosure of which is herein incorporated by reference, which in turn is a continuation in part of patent application Ser. No. 825,656, filed on Jan. 31, 1986, (now issued as U.S. Pat. No. 4,925,697) titled, "Processes for Products from Sweet Potato", the entire disclosure of which is herein incorporated by reference, as well as a continuation in part of patent application Ser. No. 294,690, filed on Aug. 1, 1988, titled, "Flour, Bread, Milk and Other Products from White Sweet Potatoes, Cassava. Edible Aroids, Amaranth, Yams and Lotus", the entire disclosure of which is herein incorporated by reference.

BACKGROUND OF THE INVENTION

(1) Field of Invention

In my previous applications listed above, I disclosed whole flours prepared from sweet potatoes, cassava, malanga and other edible aroids, amaranth, quinoa, yams, lotus, and arrowhead, as well as products prepared from them as well as manufacturing processes, as well as edible products. The present application discloses alternate processes for manufacturing these and other flours as well as the obtaining of products from flours where the sources of raw materials for the flours are obtained from any of a variety of sources of starch, soluble fibers, and insoluble fibers. These flours and products can be manufactured and used in a manner similar to those described previously for sweet potatoes, cassava, malanga and other edible aroids, amaranth, quinoa, yams, lotus, arrowhead, and others, with modification as needed to allow for differences in consistency, moisture retention, and baking properties and the like. Unless otherwise indicated, all proportions, methods of preparation and so forth are as those described in the parent applications.

The present invention is concerned with the utilization of starch insoluble fiber, and soluble fiber to form flours suitable for obtaining baked products of risen structure, and also products with colloidal properties, and other properties as described for sweet potatoes in the above referenced patent application No. 522.820 filed on May 14, 1990, and as described for sweet potatoes, cassava, malanga, yam, lotus, amaranth, quinoa, and arrowheat and others in the above referenced patent application No. 294,690 filed on Aug. 1, 1988.

The present invention is also concerned with the utilization of other root vegetables, seeds, or starchy fruits such as potatoes, arrowroot, water chestnut, jicama, buckwheat, legumes, millet, milo, barley, oats, corn, teff, rice, cotton seed meal, bread fruit, pumpkin, winter squash, white squash, plantain, banana, and jack fruit, with the purpose of producing various flours from the tubers, seeds, or starchy fruits, baked products of risen structure, and other valuable edible products and industrial products.

(2) Description of The Background

I have found that flours having properties similar to those of sweet potato and other flours described in the above referenced patent applications, may be obtained by combining the major components of the flours which may have been either obtained separately from the whole tuber vegetable, or starchy fruit, or from different sources. In other words whole flours may be used to obtain baked products of risen structure, and in addition combined flours obtained by combining starch, insoluble fiber, and soluble fiber may be used to obtain baked products of risen structure. These flours may be combined prior to baking or may be added to doughs together or at separate times during dough preparation.

SUMMARY OF THE PREFERRED EMBODIMENTS

It is one object of the present invention is to provide new flours or new combinations of ingredients, with properties similar to those of sweet potato and other whole flours described in the above referenced patent applications. These new flours or ingredient combinations may be provided by obtaining and combining separately the major components of the whole flours. In other words whole flours may be used to obtain baked products of risen structure, and in addition combined flours obtained by combining starch insoluble fiber, and soluble fiber may be used to obtain baked products of risen structure. These flours may be combined prior to baking or may be added to doughs together or at separate times during dough preparation.

The present invention is also concerned with the utilization of other root vegetables, seeds, or starchy fruits such as potatoes, arrowroot, water chestnut, jicama, buckwheat, legumes, millet, milo, barley, oats, corn, teff, rice, cotton seed meal, bread fruit, pumpkin, winter squash, white squash, plantain, banana, and jack fruit, with the purpose of producing various flours from the tubers, and other valuable edible products and industrial products.

Briefly, these objects and other objects of the present invention as hereinafter will become more readily apparent can be attained by a plurality of method embodiments which employ a flour obtained from a the above sources to prepare a variety of different foodstuffs.

DETAILED DESCRIPTION OF THE PREFERRED EMBODIMENTS

The present invention is also concerned with the utilization of root vegetables, seeds, and starchy fruits such as potatoes, arrowroot, water chestnut, jicama, buckwheat, legumes, millet, milo, barley, oats, corn, teff, rice, cotton seed meal, bread fruit, pumpkin, winter squash, white squash, plantain, banana, and jack fruit with the purpose of producing various flours from the tubers, seeds and fruit, baked products of risen structure, and other valuable edible products and industrial products.

Flours and other products may be obtained from the above roots, seeds, and starchy vegetables according to methods, procedures, and examples described in the above referenced patent applications. Unless otherwise indicated, all proportions, methods or preparation and so forth are as those described in the aforementioned patent applications.

Thus in another embodiment of the invention, dry uncooked potatoes, arrowroot, water chestnut, jicama, buckwheat, legumes, millet, milo, barley, oats, corn, teff, rice cotton seed meal, bread fruit, pumpkin, winter squash, white squash, plantain, banana, and jack fruit may each be processed to flour material by the method as described in my previous applications for sweet potatoes, cassava, edible aroids, amaranth, quinoa, yams, lotus, and arrowhead as disclosed herein above, that is, U.S. patent application Ser. No. 522,820, U.S. patent application Ser. No. 825,656 and U.S. patent application Ser. No. 294,690. The flours so produced may be used as described in the same applications as disclosed herein above.

Similarly, dried, completely or partially cooked potatoes, arrowroot, water chestnut, jicama, buckwheat, legumes, millet, milo, barley, oats, corn, teff, rice, cotton seed meal, bread fruit, pumpkin, winter, squash, white squash, plantain, banana, and jack fruit may each be processed to flour material by the method as described in my previous applications for sweet potatoes cassava, edible aroids, amaranth, quinoa, yams, lotus, and arrowhead as disclosed herein above, that is, U.S. application Ser. No. 522,820, U.S. application Ser. No. 825,656 and U.S. application Ser. No. 294,690. The flours so produced may be used as described in the same applications as described herein above.

The above flours may be used in many processes to produce desirable products.

It is within the scope of this invention to remove some of the naturally occurring fiber and substitute it with fiber from another source, e.g., cellulose or another tuber as well as adding additional fiber to that naturally occurring in a flour source, to this invention.

In another embodiment, the components of whole flours may be obtained separately and combined together to provide the properties of the whole flour. These components, such as starch, insoluble fiber, e.g., cellulose, and soluble substance such as but not limited to mucilages and gums, and dried vegetable juices may be assembled separately from materials obtained from different sources which may then be mixed together. Mixing such as milling together of such separately obtained sources of ingredients, provide the properties of the instant invention.

To prepare doughs not containing gluten from wheat or rye and yet having sufficient strength to maintain a risen structure, a starch, an insoluble fiber source, and a soluble fiber source may be utilized in the manner described in the above referenced patent applications for a whole vegetable flour ingredient. Applicant has found that these ingredients are essential to the preparation of doughs with the desired properties, when essentially gluten-free baking products are prepared.

Contrary to the teachings of the Art, when a non-wheat or non-rye starch is used in baking doughs, the addition of fiber especially fiber from plant roots or stem, enhances the ability of the doughs to trap and hold air and thus maintain a risen structure. When starch and water are combined together the starch granules tend settle out of the water and do not form a uniform mixture. When water and soluble fiber are combined, the result is a solution of dissolved solute. When water and insoluble fiber are mixed the result is a wet fibrous mat similar to wet paper pulp or wet wood pulp. Any combination of two of the three ingredients does not provide the desired properties in a baked dough. For example, when starch, insoluble fiber and water are combined and baked the result is a hard, rubbery dough mass in which whisps of fibers may be visually evident. When starch alone, or starch and soluble fibers are added to water and baked, the result is a hard, frothy mass of dried bubbles which looks and tastes like dried glue. Only when soluble fibers, insoluble fibers and starch are combined with water does the desired properties and texture of dough result.

In another embodiment of the invention, baked products having sufficient cohesive strength to maintain a risen structure may be prepared from starch, insoluble fiber, and soluble fiber by combining starch, insoluble fiber, and soluble fiber in proportions ranging from 1:0.09–1.5:0.02–0.36, and further combining these ingredients with water and baking powder or other leavening agent. Preferred ranges of starch, insoluble fiber, and soluble fiber are 1:0.25–0.6:0.03–0.3 part per unit weight.

The starch, insoluble fiber, and soluble fiber components have the properties, uses and proportions for baking and other uses which have been described in patent application Nos. 522,820 and 294,690 for whole flours of sweet potato, cassava, edible aroids, malanga, yam, amaranth, quinoa, lotus, and arrowhead. The specific ranges which apply depend upon the properties of the starch, and soluble and insoluble fibers selected for inclusion.

It is within the skill of the art to adjust the necessary proportions according to the purity of the ingredients. Thus a less pure starch may also contain some amounts of soluble and/or insoluble fibers and so require the addition of correspondingly less of these added ingredients. Similarly, it is within the skill of the Art to adjust ingredients when a soluble or insoluble fiber ingredient also contains starch and/or fibrous material.

It is also within the skill of the art to combine several starches instead of using only one starch, and/or to combine several sources of insoluble fiber instead of using only one source of insoluble fiber, and/or to combine several sources of soluble fiber instead of using only one source of soluble fiber.

Suitable starches include but are not limited to: sweet potato starch, cassava starch, malanga starch, starch from any edible aroid, yam starch, lotus starch, arrowhead starch, amaranth starch, quinoa starch, buckwheat starch, arrowroot starch, potato starch, banana starch, green bean starch, water chestnut starch, oak starch, pumpkin starch, breadfruit starch, corn starch, oat starch, millet starch, milo starch, rice starch, barley starch, jackfruit starch, jicama starch, legume starch, oat starch, teff starch, winter squash starch, white pumpkin starch, white squash starch, and plantain starch.

Suitable sources of insoluble fiber include but are not limited to: pulverized vegetable fiber obtained by filtration after water extraction, which is then purified, dried, and pulverized to a fine powder, alpha cellulose flour, bran, rice hulls, oat hulls, amaranth hulls, milo hulls, corn cobs, bean hulls, and soybean hulls. Pulverized vegetable fiber refers to the insoluble fiber obtainable particularly from root vegetables. Although pulverized vegetable fiber may be obtained from about any edible plant source including stems and leaves as well as roots, insoluble fiber obtained from root vegetables is most preferred since this fibrous material can be used in very large quantities (30% and more by weight) without imparting a gritty taste or off flavor to the final product. Pulverized roots, stems, and leaves, when obtained as described above for pulverized vegetable fiber, are preferred over pulverized seed coats.

Suitable sources of soluble fiber include but are not limited to: dried, pulverized vegetable juices obtained from pulverized root or other vegetables, seeds, roots, or starchy fruits by pressing, filtration, and starch removal by centrifugation or by water extraction and subsequent starch removal or by other suitable methods; sodium carboxymethylcellulose, hydroxymethylcellulose, guar gum, tragacanth gum, karaya gum, algin, agar, carrageenan, and other mucilages and gums.

Having generally described this invention, a further understanding can be obtained by reference to certain specific examples which are provided herein for purposes of illustration only and are not intended to be limiting unless otherwise specified.

EXAMPLE NUMBER 1

BREAD PRODUCT FROM STARCH, INSOLUBLE FIBER AND SOLUBLE FIBER

Combine 0.24 lb white sweet potato starch, 0.09 lb of the dried, pulverized insoluble fiber from white sweet potato, and 0.02 lb dried, pulverized soluble fiber from white sweet potato, and mix well. Then add 0.53 lb water and 0.03 lb baking powder and mix thoroughly. Place in baking pan and bake for 25 minutes at 425° F. Soluble fiber and insoluble fiber were obtained as described in Rule 132 Declaration of Karen M. Slimak, on May 4, 1988, published as part of the file of U.S. Pat. No. 4,925,697, and herein incorporated by reference.

EXAMPLE 2

BREAD PRODUCT FROM STARCH, INSOLUBLE FIBER AND SOLUBLE FIBER

Combine 0.24 lb arrowroot starch, 0.09 lb of the dried, pulverized insoluble fiber from white sweet potato, and 0.02 lb dried, pulverized soluble fiber from cassava, and mix well. Then add 0.53 lb water and 0.03 lb baking powder and mix thoroughly. Place in baking pan and bake for 25 minutes at 425° F. Soluble fiber and insoluble fiber were obtained as described in Rule 132 Declaration of Karen M. Slimak, on May 4, 1988, published as part of the file of U.S. Pat. No. 4,925,697, and herein incorporated by reference.

EXAMPLE 3

POTATO FLOUR

Thinly peel potatoes under running water, removing any spots, and other undesirable areas; rinse briefly in distilled water; remove excess water; do not soak. Shred to desired size, place on glass or metal trays; air dry at 145° F. for 8-12 hours, preferably 10 hrs. Comminute shreds into a moderately fine flour product.

EXAMPLE 4

COOKED POTATO FLOUR

The method of example 4 is used to produce a cooked flour product, with the added process of heating the potato with steam until gelatinized, and then proceeding with shredding and drying steps.

EXAMPLE 5

BREADFRUIT FLOUR

Peel firm, green breadfruit under running water, removing any spots, and other undesirable areas; rinse briefly in distilled water; remove excess water; do not soak. Shred to desired size, place on glass or metal trays; air dry at 145° F. for 8-12 hours, preferably 10 hrs. Comminute shreds into a moderately fine flour product.

EXAMPLE 6

COOKED BREADFRUIT FLOUR

The method of example 6 is used to produce a cooked flour product, with the added process of heating the breadfruit with steam until gelatinized, and then proceeding with shredding and drying steps.

EXAMPLE 7

ARROWROOT FLOUR

Thinly peel arrowroot under running water, removing any spots, and other undesirable areas; rinse briefly in distilled water; remove excess water; do not soak. Shred to desired size, place on glass or metal trays; air dry at 145° F. for 8-12 hours, preferably 10 hrs. Comminute shreds into a moderately fine flour product.

EXAMPLE 8

COOKED ARROWROOT FLOUR

The method of example 8 is used to produce a cooked flour product, with the added process of heating the arrowroot with steam until gelatinized, and then proceeding with shredding and drying steps.

EXAMPLE 9

WATER CHESTNUT FLOUR

Thinly peel water chestnuts under running water, removing any spots, and other undesirable areas; rinse briefly in distilled water; remove excess water; do not soak. Shred to desired size, place on glass or metal trays; air dry at 145° F. for 8-12 hours, preferably 10 hrs. Comminute shreds into a moderately fine flour product.

EXAMPLE 10

COOKED WATER CHESTNUT FLOUR

The method of example 10 is used to produce a cooked flour product, with the added process of heating the water chestnut with steam until gelatinized, and then proceeding with shredding and drying steps.

Having now fully described the invention, it will be apparent to one of ordinary skill in the art that many changes and modifications can be made thereto without departing from the spirit of the invention as set forth herein.

What is claimed as new and so intended to be secured by Letters Patent is:

1. An edible flour,
consisting essentially of comminuted particles obtained from separate sources,
said sources consisting essentially of a source of starch, soluble fiber, and of insoluble fiber,
said source of starch selected from the group consisting of sweet potato, cassava, edible aroids, malanga, yam, amaranth, quinoa, lotus, arrowhead, potatoes, arrowroot, water chestnut, jicama, buckwheat, green bean, legumes, oak, millet, milo, barley, oats, corn, teff, rice, cotton seed meal, breadfruit, pumpkin, winter squash, white pumpkin, white squash, plantain, banana, and jack fruit,
said source of soluble fiber selected from the group consisting of dried, pulverized vegetable juices, mucilages, gums, sodium carboxymethylcellulose, hydroxymethylcellulose, guar gum, tragacanth gum, karaya gum, algin, agar, and carrageenan, and
said source of insoluble fiber selected from the group consisting of vegetable fiber, alpha cellulose flour, bran, rice hulls, amaranth hulls, milo hulls, corn cobs, bean hulls, and soybean hulls, said flour comminuted to a size so that substantially all of said flour passes through a screen of 0.015 inch opening, said flour having a moisture content of less than 20%, and wherein said flour possesses the ability to maintain a risen structure in the absence of gluten.

2. The flour of claim 1 wherein the starch, soluble fiber and insoluble fiber are selected from the group consisting of sweet potato, cassava, edible aroids, malanga, yam, amaranth, quinoa, lotus, arrowhead, potatoes, arrowroot, water chestnut, jicama, buckwheat, legumes, millet, milo, barley, oats, corn, teff, cotton seed meal, breadfruit, pumpkin, winter squash, white squash, plantain, banana, and jack fruit, wherein the source of starch, soluble fiber and insoluble fiber is not selected from a single member of said group.

3. An edible, whole flour product consisting essentially of tubers, seeds or starchy fruits, selected from the group consisting of potatoes, arrowroot, water chestnut, jicama, buckwheat, legumes, millet, milo, barley, oats, corn, teff, cotton seed mean, breadfruit, pumpkin, winter squash, white squash, plantain, banana, and jack fruit, wherein the flour consists essentially of the starch, soluble fiber and insoluble fiber portions of the tuber, seed or starchy fruit, comminuted to a size so that substantially all of said comminuted tuber, seed or starchy fruit passes through a screen of 0.015 inch mesh opening, said flour having a moisture content of less than 20% by weight, wherein said edible whole flour product possesses the ability to maintain a risen structure in the absence of gluten or chemical modifiers.

4. The flour of claim 3 wherein the flour is from potatoes of the family Solonaceae.

5. The flour of claim 3 wherein the flour is from water chestnut.

6. The flour of claim 3 wherein the flour is from arrowroot.

7. The flour of claim 3 wherein the flour is from breadfruit.

8. The flour of claim 3 wherein at least one of said portions of the flour is obtained from a separate source of said tubers, seeds or starchy fruits.

9. The flour of claim 3 wherein substantially all of the flour passes through a screen opening of 0.001 inch.

10. A milk substitute comprising water and the flour of claim 3 in amounts effective to produce said milk substrate.

11. An infant formula comprising the flour of claim 10, and water in amounts effective to produce said infant formula.

12. An ice cream substitute formed by freezing the milk substitute of claim 10.

13. An imitation nut butter product comprising oil and the flour of claim 3 in amounts effective to produce said nut butter substitute.

14. A baked product comprising the flour of claim 3 water, and leavening agent, in amounts effective to produce said baked product.

15. An extruded product comprising water and the flour of claim 3 in amounts effective to produce said extruded product.

16. A colloidal product comprising the flour of claim 3 an oil; and water, in amounts effective to produce said colloidal product.

17. A fried product comprising the flour of claim 3 an oil; and water, in amounts effective to produce said fried product.

18. A batter-type product comprising the flour of claim 3 an oil; and water, in amounts effective to produce said batter-type product.

* * * * *